United States Patent
Payne

(10) Patent No.: US 8,109,964 B2
(45) Date of Patent: Feb. 7, 2012

(54) DEVICE FOR COMPRESSION OF TISSUE UNDER THE EYES

(76) Inventor: Richard A. Payne, Greenwood, IN (US)

(*) Notice: Subject to any disclaimer, the term of this patent is extended or adjusted under 35 U.S.C. 154(b) by 532 days.

(21) Appl. No.: 10/941,232

(22) Filed: Sep. 15, 2004

(65) Prior Publication Data

US 2006/0058840 A1  Mar. 16, 2006

(51) Int. Cl.
*A61F 9/04* (2006.01)
(52) U.S. Cl. .................................. 606/204.25; 607/109
(58) Field of Classification Search .................. 606/201, 606/204.25; 607/109, 112, 114; 2/2, 171.2; 604/114
See application file for complete search history.

(56) References Cited

U.S. PATENT DOCUMENTS

| | | | | |
|---|---|---|---|---|
| 1,917,117 A | * | 7/1933 | Hines ................................. | 2/15 |
| 2,874,385 A | | 2/1959 | Wade | |
| 3,354,884 A | | 11/1967 | Rudo | |
| 4,326,533 A | * | 4/1982 | Henderson .................... | 607/112 |
| 4,372,318 A | * | 2/1983 | Viesturs et al. ............... | 607/109 |
| 5,188,103 A | | 2/1993 | Smith | |
| 5,274,865 A | * | 1/1994 | Takehashi ......................... | 5/644 |
| 5,277,700 A | | 1/1994 | Smith | |
| 5,343,561 A | * | 9/1994 | Adamo .............................. | 2/15 |
| 5,666,671 A | | 9/1997 | Daneshvar | |
| 5,700,238 A | | 12/1997 | Hyson | |
| 5,713,078 A | * | 2/1998 | DeAngelis ...................... | 2/209 |
| 5,823,984 A | | 10/1998 | Silverberg | |
| 5,961,479 A | | 10/1999 | Reeves et al. | |
| D465,234 S | * | 11/2002 | Gordon ....................... | D16/301 |
| 6,537,308 B2 | * | 3/2003 | Burkhart ...................... | 607/109 |
| 6,623,517 B1 | * | 9/2003 | DeLuisa et al. ............... | 607/109 |

* cited by examiner

*Primary Examiner* — Kathleen Sonnett
(74) *Attorney, Agent, or Firm* — Woodard, Emhardt, Moriarty, McNett & Henry, LLP

(57) ABSTRACT

Described is a device useful for applying compression to the eyes and regions under the eyes of a user. In one form, such a compression device includes a relatively elongate compression body combined with a strap for receipt around the head of a user. The relatively elongate compression body includes a central region for receipt over the face of a user, as well as flanking regions for receipt over the side of the face and the ears of the user, substantially encircling the head. Preferred devices include compression bodies having pockets containing compression inserts and positioned to contact the eyes and under-eye tissues of the user, desirably having openings in a location other than at an edge of the pockets, e.g. provided by a central slit. Compression inserts may include foam pads or conformable membrane shells encasing a flowable fluid or other substance.

14 Claims, 3 Drawing Sheets

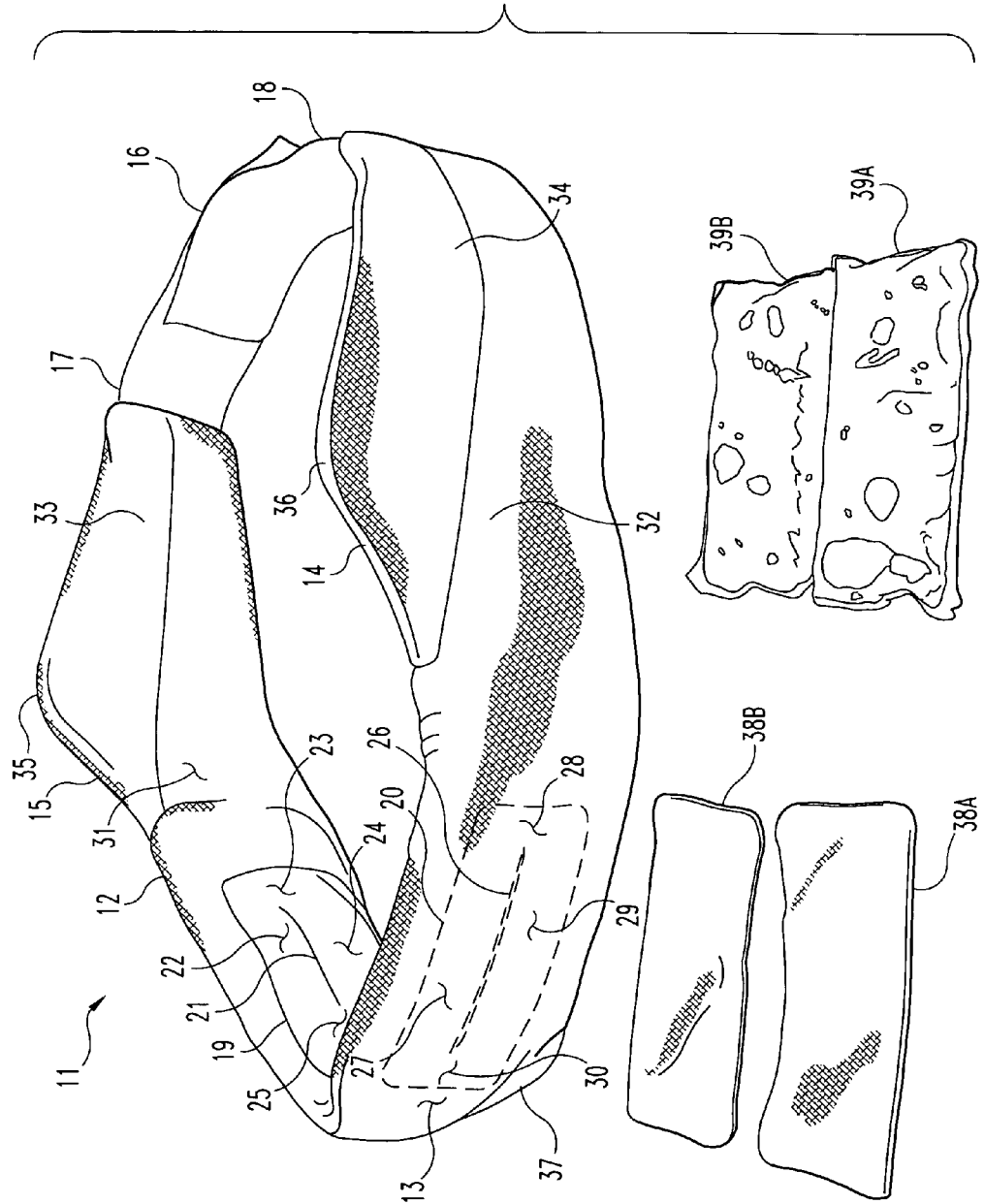

DEVICE FOR COMPRESSION OF TISSUE UNDER THE EYES

BACKGROUND OF THE INVENTION

The present invention relates generally to compression devices, and in particular to a device that is useful for applying compression to tissue regions occurring underneath the eyes of a human.

As further background, a number of devices and methods have been suggested for use in applying compression to areas of the face, including areas in and around the eyes. Examples of such devices are found, for example, in U.S. Pat. Nos. 5,700,238, 6,193,740, and 6,537,308. Because the face, and in particular the regions around the eyes, can be quite sensitive to abrasion, scraping, or other sources of injury or discomfort, it is important that devices for compressing these areas be well designed to be both effective for compressing the desired regions while also comfortable to the user. The present invention is addressed to these needs.

SUMMARY OF THE INVENTION

In one aspect, the present invention provides a device useful for compression of facial tissues occurring under the eyes of a human. In accordance with the invention, the device includes a compression body having a generally elongate shape. The compression body has a central portion for covering tissues under the eyes of a user, and flanking portions flanking the central portion and configured to cover ears of the user. In preferred forms, the flanking portions generally have a maximum width greater than the maximum width of the central portion and dimensions so as to cover essentially the entire ears of the user. The central portion of the compression body includes first and second pockets for receiving compression inserts. These pockets are located on an interior side of the central portion and positioned to each cover a region under an eye of the user. The device also includes a strapping mechanism connected to the compression body, useful for strapping the body around the head of the user.

In another embodiment, the present invention provides a device useful for the compression of facial tissues occurring under the eyes of a human. In accordance with this embodiment, the device includes a conformable compression body having a generally elongate shape. The compression body is configured to cover tissues under the eyes of a user. The compression body further includes first and second pockets for receiving compression inserts. These pockets are located to position a compression insert received therein over a region under an eye of a user without substantial overlap of an overlying brow ridge of the user. The device further includes a strap connected to the compression body useful for strapping the body around the head of the user.

Desirably, pockets included in devices of the invention are relatively narrow and elongate, and generally rectangular in shape. In certain embodiments, the compression inserts received within the pockets are conformable containers containing a flowable substance such as a liquid or gel. In other embodiments, the compression inserts are pads, pillows, or other similar articles made of compressible material. Pockets included in devices of the invention desirably include an opening located generally in the middle of the pocket, as opposed to at an edge thereof. In this fashion, compression inserts received within the pockets are less likely to have edges that contact and scrape or otherwise irritate tissues of the user.

Additional embodiments as well as features and advantages of the invention will be apparent from the further descriptions herein.

BRIEF DESCRIPTION OF THE FIGURES

FIG. 1 provides a perspective view of a device of the invention along with compression inserts useful therein.

DETAILED DESCRIPTION

Figure 1A:
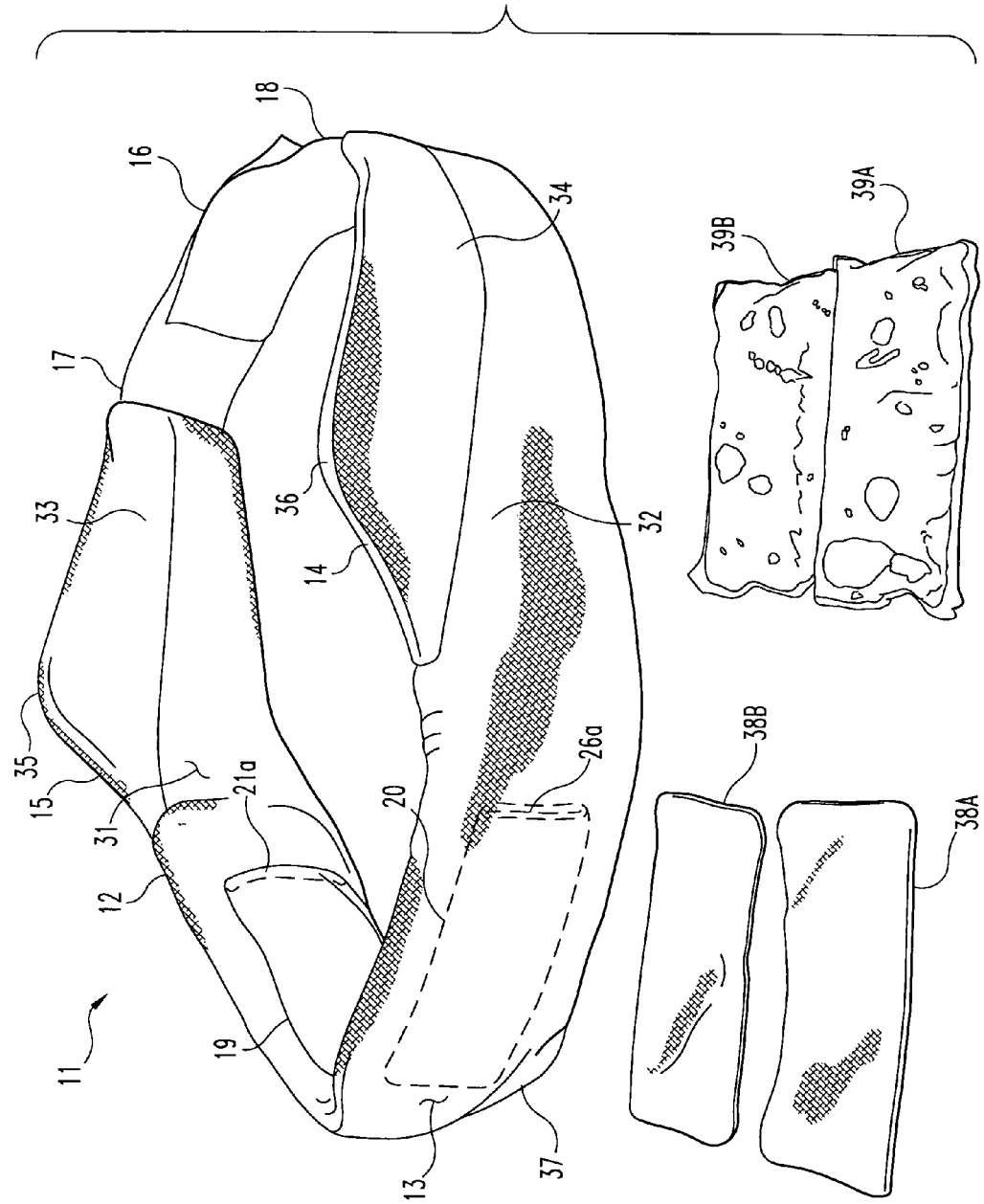
FIG. 1A provides a perspective view of an alternate device of the invention.

For the purposes of promoting an understanding of the principles of the invention, reference will now be made to the embodiments illustrated in the drawings and specific language will be used to describe the same. It will nevertheless be understood that no limitation of the scope of the invention is thereby intended, and alterations and modifications in the illustrated device, and further applications of the principles of the invention as illustrated therein are herein contemplated as would normally occur to one skilled in the art to which the invention relates.

As disclosed above, in one aspect, the present invention provides a device that is useful for applying compression to regions under the eyes of a user. Devices of the invention include a relatively elongate compression body that includes first and second pockets for receiving compression inserts. The pockets and inserts are configured to selectively compress areas of the face including the eyes and regions occurring immediately below the eyes, for example to diminish the presence of fluids or other causes of puffiness in these areas, which result in what are commonly referred to "bags" under the eyes.

With reference now to FIG. 1, shown is a perspective view of a compression device 11 of the invention, along with compression inserts therefore. Device 11 includes a compression body 12 that generally includes a central region 13 for receipt over top the face of a user, and flanking regions 14 and 15 bounding the central region 13. Flanking regions 14 and 15 will be received overtop the ears of a user, and thus compression body 12 as a whole resembles a hoop or "U" shape that is received substantially around the head of a user, covering the eyes and ears of the user. Device 11 also includes a strap 16 connected to the compression body 12, for receipt around the back of the head of a user to retain the device 11 in place. Desirably, strap 16 is made of separate segments 17 and 18 that are connectable at various locations along their length, so that the level of compression applied by the compression body 12 can be adjusted. In this regard, the connection between strap segments 17 and 18 can be achieved in a suitable fashion. Illustratively, a "hook and loop" connection such as provided by Velcro brand fasteners can be used. Alternatively, an adjustable connection can be achieved by a series of apertures located in segment 17 and one or more corresponding pegs in strap segment 18 dimensioned for a snug friction fit in the apertures, as is common in baseball or other sporting caps. These and other attachment mechanisms may be used in the present invention without departing from its scope.

Central portion 13 of compression body 12 includes a first pocket 19 and a second pocket 20 (shown in phantom) that are configured for receipt of a compression insert. In alternative forms of the invention, compression members may be provided integral with or attached to compression body 12 generally in the location of pockets 19 and 20. In the preferred device, however, pockets 19 and 20 are provided and include respective openings 21 and 26 for enabling insertion of compression elements within the pockets 19 and 20. With reference particularly now to pocket 19, opening 21 is provided as an elongate slit located in an internal region of the pocket rather than at an edge thereof. Thus, slit 21 is bounded by upper and lower material regions 22 and 24, as well as lateral material regions 23 and 25. Pocket 20 is provided similarly with upper and lower material regions 27 and 29 and lateral material regions 28 and 30. Such configurations are particularly advantageous for pockets 19 and 20. In this manner, a user will be relatively protected from contact with edges of compression inserts received within pockets 19 and 20. Rather, contact, if any, with a compression insert will generally occur in a central, non-edge region of the insert which will in many cases be less irritating than contact with an edge of the insert.

The preferred compression body 12 of device 11 includes flanking regions 14 and 15 having a maximum width that is greater than a maximum width of the central region 13. In the illustrative device 11, flanking region 14 includes segments 32 and 34 with diverging outer walls thus varying in width, bounding a widest portion 36. Flanking region 15 is similarly configured with diverging regions or segments 31 and 33 located on either side of a widest region 35. As shown in the illustrated device, this diverging thickness in the flanking portions may be provided in a configuration wherein the lower edges of flanking portions 14 and 15 are generally coplanar with the lower edge of central region 13, whereas upper edges of flanking regions 14 and 15 diverge from a coplanar relationship with upper edge of central region 13 generally reaching an apex at the widest portions 35 and 36. The wider flanking regions 14 and 15 are preferably dimensioned to cover at least substantially the entire ears of a user which results in increased comfort and also some sound dampening for a user wearing device 11. Also, central region 13 of device 11 may include a nose piece 37 adapted for receipt over the bridge of the nose of a user. Portion 37 may be deflectable relative to the remainder of central region 13 to facilitate a close fit of adjacent regions to the eyes and under-eye regions of the user.

Also shown in FIG. 1 are compression inserts that may be used with device 11. A first pair of compression inserts 38A and 38B may be formed from a solid material such as cloth or a polymer foam. Also shown is a second style of compression insert, including inserts 39A and 39B which include a conformable, sealed membrane bag containing a liquid or other flowable substance. The enclosed fluid may, for example, include a gel or other material designed to retain heat or coolness imparted thereto, for application of a temperature treatment to the facial tissues of the user.

The elements of device 11 and compression inserts therefore may be constructed of any suitable material. Typically, compression body 12 will be formed from a relatively soft, non-irritating material. Suitable materials for these purposes include but are not limited to cotton, silk, nylon, stain, wool, or other natural or synthetic, woven or non-woven materials that form a flexible, translucent or opaque barrier.

Figure 2:
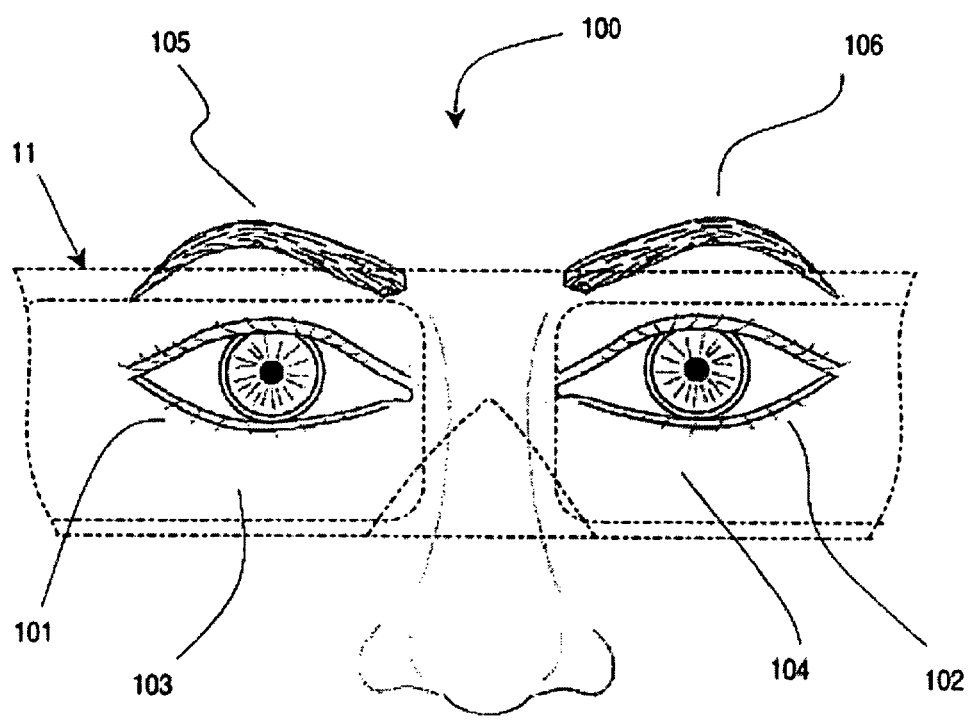
FIG. 2 provides a perspective view of a portions of a device of the invention positioned upon the face of a user.

Referring now also to FIG. 2, provided is an illustration of the device 11 (partially cutaway) positioned upon the face of a user 100. Device 11 is shown with its pocket regions 19 and 20 positioned generally over the eyes of the user, covering and compressing both ocular regions 101 and 102 as well as tissue regions 103 and 104 occurring immediately thereunder. The preferred device 11 has a relatively narrow profile as it traverses the eye regions of a user, and thus does not substantially overlap the brows 105 and 106 and associated brow ridge of the user. This facilitates an improved ability to compress tissues in and around the eyes of the user, particularly areas immediately above the eyes that might be shielded from all or a part of the desired compression if the device 11 had portions overlapping and supported by the brow ridge and was not otherwise sufficiently conformable to effectively contact and compress these areas. In addition to the device 11 position shown in FIG. 2, device 11 can be worn so as to only cover the tissue regions 103 and 104 below the eyes of the user, and to leave the eyes of the user unobstructed so that the user's vision is intact. A relatively narrow profile of the central portion 13 of the device 11 and of the compression inserts 38A, 38B or 39A, 39B facilitates this mode of use.

Now referencing FIG. 1A, shown is a perspective view of another compression device of the present invention. Device 11 as illustrated in FIG. 1A is similar in construction to that depicted in FIG. 1, except in the pocket areas. In particular, pockets 19 and 20 of FIG. 1A include slit openings 21a and 26a that are located at the outer edge of the pockets 19 and 20, respectively. In this manner, the compression inserts 38A and 38B or 39A and 39B can be pushed into and removed from the openings 21a and 26a at the outer edges of the pockets.

While the invention has been described in detail above with reference to specific embodiments, it will be understood that modifications and alterations in the embodiments disclosed may be made by those practiced in the art without departing from the spirit and scope of the invention. All such modifications and alterations are intended to be covered. In addition, all publications cited herein are indicative of the abilities of those of ordinary skill in the art and are hereby incorporated by reference in their entirety as if each had been individually incorporated by reference and fully set forth.

What is claimed is:

1. A device useful for compression of facial tissues occurring under the eyes of a human, the device comprising:
    (a) a conformable compression body having a generally elongate shape;
        said compression body having a central portion for covering tissues under the eyes of a user, and flanking portions flanking the central portion and configured to cover ears of the user;
    wherein said central portion has an upper edge, a lower edge, and a length sized to span from an outside of one eye of the user, across the nose of the user, and to an outside of another eye of the user, wherein said upper edge and lower edge of said central portion are generally straight all along said length, and further wherein said central portion has a width profile between said upper edge and said lower edge that is sufficiently narrow such that the central portion traverses an eye regions of the user without substantial overlap of overlying brow ridges of the user;
        said flanking portions each having a point of maximum width greater than a point of maximum width of said central portion, and sufficiently dimensioned to cover the entire ears of the user;
        said flanking portions each having diverging widths located on either side of said point of maximum width;
        said flanking portions each having a lower edge that is generally coplanar with the lower edge of said central portion;
        said compression body including first and second pockets for receiving compression inserts, said first and second pockets each located in a fixed position relative to said central portion, said first and second pockets each located to position a compression insert received therein over a region under an eye of a user without substantial overlap of an overlying brow ridge, and said first and second pockets having respective first and second upper pocket edges, said upper pocket edges being substantially straight and each extending substantially parallel to said upper edge of said central portion; and (b) a strap connected to the compression body, for strapping the compression body around the head of the user.

2. The device of claim 1, wherein said pockets are each generally elongate, and wherein the long axis of each pocket is positioned generally horizontally.

3. The device of claim 2, also including first and second elongate compression inserts received within said first and second pockets, respectively.

4. The device of claim 3, wherein said pockets each include a perimeter edge connected to the compression body, and an elongate opening spaced from the perimeter edge.

5. The device of claim 1, wherein the strap includes first and second strap segments attached to the compression body, said first and second strap segments connectable to one another at varying locations along their length.

6. The device of claim 1, wherein said compression body is hoop shaped for receipt around the head of the user.

7. The device of claim 1, wherein said flanking portions each include a first segment attached to a second segment, wherein said first segment is co-extensive with said central portion and provides said lower edge of said flanking portion, and wherein said second segment is positioned above said first segment and provides an upper edge of said flanking portion.

8. A device useful for compression of facial tissues occurring under the eyes of a human, the device comprising:

(a) a conformable compression body having a hoop shape configured for receipt around the head of a human user;
said compression body having a central portion for covering tissues under the eyes of a user, and flanking portions flanking the central portion and configured to cover ears of the user;
said central portion being generally rectangular in shape and having a width profile sufficiently narrow such that the central portion traverses an eye regions of the user without substantial overlap of the central portion onto overlying brow ridges of the user;
said flanking portions each having a point of maximum width greater than a point of maximum width of said central portion, and sufficiently dimensioned to cover the entire ears of the user;
said flanking portions each having diverging widths located on either side of said point of maximum width;
said flanking portions each including a first segment attached to a second segment, wherein said first segment is co-extensive with said central portion and provides a lower edge of said flanking portion, and wherein said second segment is positioned above said first segment and provides an upper edge of said flanking portion;
said compression body including first and second generally rectangular pockets for receiving compression inserts, said first and second pockets each located to position a compression insert received therein over a region under an eye of a user without substantial overlap of an overlying brow ridge; and (b) a strap connected to the compression body, for strapping the compression body around the head of the user.

9. The device of claim 8, wherein said pockets are each generally elongate, and wherein the long axis of each pocket is positioned generally horizontally.

10. The device of claim 9, also including first and second elongate compression inserts received within said first and second pockets, respectively.

11. The device of claim 8, wherein said pockets each include a perimeter edge connected to the compression body, and an elongate opening spaced from the perimeter edge.

12. The device of claim 8, wherein the strap includes first and second strap segments attached to the compression body, said first and second strap segments connectable to one another at varying locations along their length.

13. The device of claim 8, wherein:
said central portion has an upper edge, a lower edge, and a length sized to span from an outside of one eye of the user, across the nose of the user, and to an outside of another eye of the user, and wherein said upper edge and lower edge of said central portion are generally straight all along said length;
said flanking portions each have diverging widths located on either side of said point of maximum width; and
said flanking portions each have a lower edge that is generally coplanar with the lower edge of said central portion.

14. A device useful for compression of facial tissues occurring under the eyes of a human, the device comprising:

(a) a conformable compression body having a generally elongate shape;
said compression body having a central portion for covering tissues under the eyes of a user, and flanking portions flanking the central portion and configured to cover ears of the user;
said central portion having an upper edge, a lower edge, and a length sized to span from an outside of one eye of the user, across the nose of the user, and to an outside of another eye of the user, wherein said upper edge and lower edge of said central portion are generally straight and parallel to one another all along said length, and further wherein said central portion has a width profile between said upper edge and lower edge that is sufficiently narrow such that the central portion traverses the an regions of the user without substantial overlap of the central portion onto overlying brow ridges of the user;
said flanking portions each having a point of maximum width greater than a point of maximum width of said central portion, and sufficiently dimensioned to cover the entire ears of the user;
said flanking portions each having diverging widths located on either side of said point of maximum width;
said flanking portions each having a lower edge that is generally coplanar with a lower edge of said central portion;
said flanking portions each including a first segment attached to a second segment, wherein said first segment is co-extensive with said central portion and provides said lower edge of said flanking portion, and wherein said second segment is positioned above said first segment and provides an upper edge of said flanking portion;
said compression body including first and second elongate, generally rectangular pockets for receiving compression inserts, said first and second pockets each located to position a compression insert received therein over a region under an eye of a user without substantial overlap of an overlying brow ridge, and wherein the long axis of each pocket is positioned generally horizontally;
(b) first and second elongate, generally rectangular compression inserts received within said first and second pockets, respectively; and
(c) a strap connected to the compression body, for strapping the compression body around the head of the user.

* * * * *